US008637041B2

(12) United States Patent
Guerry-Kopecko et al.

(10) Patent No.: US 8,637,041 B2
(45) Date of Patent: Jan. 28, 2014

(54) **SECRETED *CAMPYLOBACTER* FLAGGELLA COREGULATED PROTEINS AS IMMUNOGENS**

(75) Inventors: Patricia Guerry-Kopecko, Silver Spring, MD (US); Shahida Baqar, Olney, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/526,610

(22) Filed: Jun. 19, 2012

(65) Prior Publication Data

US 2013/0017215 A1 Jan. 17, 2013

Related U.S. Application Data

(62) Division of application No. 11/800,955, filed on May 8, 2007, now Pat. No. 8,221,764.

(60) Provisional application No. 60/800,099, filed on May 12, 2006.

(51) Int. Cl.
*A61K 39/00* (2006.01)
*A61K 39/02* (2006.01)
*C07K 1/00* (2006.01)

(52) U.S. Cl.
USPC ...................... 424/185.1; 424/234.1; 530/350

(58) Field of Classification Search
None
See application file for complete search history.

(56) References Cited

U.S. PATENT DOCUMENTS

| | | | |
|---|---|---|---|
| 6,987,176 B1 | 1/2006 | Guerry et al. | |
| 8,221,764 B2 * | 7/2012 | Guerry-Kopecko et al. | 424/185.1 |
| 2004/0006037 A1 | 1/2004 | Chan et al. | |

OTHER PUBLICATIONS

Parkhill et al (Nature vol. 403, pp. 665-668, 2000).*
Deutsch et al (Journal of Biological Chemistry vol. 266, No. 24, pp. 16021-16028, 1991).*
Wu et al (Infection and Immunity vol. 62, No. 10, pp. 4256-4260, 1994).*
Fouts, Derrick E. et al. Major Structural Differences and Novel Potential Virulence Mechanishms from the Genomes of Multiple *Compylobacter* Species. 2005. PLoS Biol. 3(1) e15, pp. 72-85 www.plosbiology.org.

* cited by examiner

*Primary Examiner* — Albert Navarro
(74) *Attorney, Agent, or Firm* — Ning Yang; Gilbert M. Churilla; Joseph K. Hemby

(57) ABSTRACT

The invention relates to an immunogenic composition composed of secreted polypeptides derived from *Campylobacter jejuni* non-flagellar proteins that are coordinately expressed with the flagellar regulon. The invention also relates to a method of inducing an immune response to the non-flagellar protein polypeptides.

17 Claims, 7 Drawing Sheets

A.

B.

A.

B.

SEQUENCE LISTING

```
<160> NUMBER OF SEQ ID NOS: 19

<210> SEQ ID NO 1
<211> LENGTH: 429
<212> TYPE: DNA
<213> ORGANISM: Campylobacter jejuni

<400> SEQUENCE: 1

atgcaaatta acaattcctt aaatagctta agtcaatatg ttaaagtcaa cttaaacgaa      60

gaaaatcaaa actctaaaaa tcaagaacaa aatgctttag cgcaagatcc agctgtagag     120

gtaaatatca gcaaagaagc caaagaaaaa tcaaatactt ctaatcaaaa caattctcaa     180

gctccagctc aagctttaaa cgcacaaaac aacacgcaac aaaatagtag tagcaatagt     240

gaagataaac ttacagaatt aacacaaaag cttgcagaaa ttcaagcaaa aattgttgaa     300

ctaactgcaa aaatgtctaa agctaatgag gatcaaatca aaagtattga aagtcaaata     360

gcaacattaa atgcccaagc ttcaactatt caagctcaaa ttcaagaact ccaaagtcaa     420

caagcttga                                                             429


<210> SEQ ID NO 2
<211> LENGTH: 142
<212> TYPE: PRT
<213> ORGANISM: Campylobacter jejuni
```

-continued

<400> SEQUENCE: 2

```
Met Gln Ile Asn Asn Ser Leu Asn Ser Leu Ser Gln Tyr Val Lys Val
1               5                   10                  15

Asn Leu Asn Glu Glu Asn Gln Asn Ser Lys Asn Gln Glu Gln Asn Ala
            20                  25                  30

Leu Ala Gln Asp Pro Ala Val Glu Val Asn Ile Ser Lys Glu Ala Lys
        35                  40                  45

Glu Lys Ser Asn Thr Ser Asn Gln Asn Asn Ser Gln Ala Pro Ala Gln
    50                  55                  60

Ala Leu Asn Ala Gln Asn Asn Thr Gln Gln Asn Ser Ser Ser Asn Ser
65                  70                  75                  80

Glu Asp Lys Leu Thr Glu Leu Thr Gln Lys Leu Ala Glu Ile Gln Ala
                85                  90                  95

Lys Ile Val Glu Leu Thr Ala Lys Met Ser Lys Ala Asn Glu Asp Gln
            100                 105                 110

Ile Lys Ser Ile Glu Ser Gln Ile Ala Thr Leu Asn Ala Gln Ala Ser
        115                 120                 125

Thr Ile Gln Ala Gln Ile Gln Glu Leu Gln Ser Gln Gln Ala
    130                 135                 140
```

<210> SEQ ID NO 3
<211> LENGTH: 429
<212> TYPE: DNA
<213> ORGANISM: Campylobacter jejuni

<400> SEQUENCE: 3

```
atgaaaatag atactttgac aaaaaatttt agcaattatc aaacacaaat aaacaaagac     60

aatgatttgg taagtaatgt tcatagcgac aatgtggtta aaattcaaat ttcagatgaa    120

gcaagaagtt taagtcaaac aaattcaaaa aatgaaaaag aatatgaaat caaagtaagt    180

caagaaaaaa tagaaaacca caaagaccaa aattccattc aaaatagcaa aggtggcgta    240

aatcccgcat tagaggcttt aatagcaaaa ttagctgaaa ttttagctaa aattgcagaa    300

cttactcaaa aaatgacaaa cgctaacgaa caaatgaaaa cgacatttca aaaacaaatt    360

gatgtgctaa aatctcaagc agatgtaatt caagctcaaa ttcaagaact ccaaagccaa    420

caagcttga                                                            429
```

<210> SEQ ID NO 4
<211> LENGTH: 142
<212> TYPE: PRT
<213> ORGANISM: Campylobacter jejuni

<400> SEQUENCE: 4

```
Met Lys Ile Asp Thr Leu Thr Lys Asn Phe Ser Asn Tyr Gln Thr Gln
1               5                   10                  15

Ile Asn Lys Asp Asn Asp Leu Val Ser Asn Val His Ser Asp Asn Val
            20                  25                  30

Val Lys Ile Gln Ile Ser Asp Glu Ala Arg Ser Leu Ser Gln Thr Asn
        35                  40                  45

Ser Lys Asn Glu Lys Glu Tyr Glu Ile Lys Val Ser Gln Glu Lys Ile
    50                  55                  60

Glu Asn His Lys Asp Gln Asn Ser Ile Gln Asn Ser Lys Gly Gly Val
65                  70                  75                  80

Asn Pro Ala Leu Glu Ala Leu Ile Ala Lys Leu Ala Glu Ile Leu Ala
                85                  90                  95
```

-continued

```
Lys Ile Ala Glu Leu Thr Gln Lys Met Thr Asn Ala Asn Glu Gln Met
            100                 105                 110

Lys Thr Thr Phe Gln Lys Gln Ile Asp Val Leu Lys Ser Gln Ala Asp
        115                 120                 125

Val Ile Gln Ala Gln Ile Gln Glu Leu Gln Ser Gln Gln Ala
    130                 135                 140
```

<210> SEQ ID NO 5
<211> LENGTH: 28
<212> TYPE: DNA
<213> ORGANISM: Campylobacter jejuni

<400> SEQUENCE: 5
cctatttatg gattgcaatt tcaccccg 28

<210> SEQ ID NO 6
<211> LENGTH: 26
<212> TYPE: DNA
<213> ORGANISM: Campylobacter jejuni

<400> SEQUENCE: 6
cttgaaacga tcaagggtag ggcagc 26

<210> SEQ ID NO 7
<211> LENGTH: 39
<212> TYPE: DNA
<213> ORGANISM: Campylobacter jejuni

<400> SEQUENCE: 7
gacgacgaca agatgcaaat taacaattcc ttaaatagc 39

<210> SEQ ID NO 8
<211> LENGTH: 39
<212> TYPE: DNA
<213> ORGANISM: Campylobacter jejuni

<400> SEQUENCE: 8
gaggagaagc ccggttcaag cttgttggct ttggagttc 39

<210> SEQ ID NO 9
<211> LENGTH: 31
<212> TYPE: DNA
<213> ORGANISM: Campylobacter jejuni

<400> SEQUENCE: 9
ccatatgcaa attaacaatt ccttaaatag c 31

<210> SEQ ID NO 10
<211> LENGTH: 31
<212> TYPE: DNA
<213> ORGANISM: Campylobacter jejuni

<400> SEQUENCE: 10
gggatcctca agcttgttgg ctttggagtt c 31

<210> SEQ ID NO 11
<211> LENGTH: 37
<212> TYPE: DNA
<213> ORGANISM: Campylobacter jejuni

<400> SEQUENCE: 11
cgggatccca ccgctaatag cccaaaaaat acctccc 37

-continued

<210> SEQ ID NO 12
<211> LENGTH: 39
<212> TYPE: DNA
<213> ORGANISM: Campylobacter jejuni

<400> SEQUENCE: 12
ggaattccgc aagtatactt gaaacgatca agggtaggg 39

<210> SEQ ID NO 13
<211> LENGTH: 498
<212> TYPE: DNA
<213> ORGANISM: Campylobacter jejuni

<400> SEQUENCE: 13
atgggccatc atcatcatca tcatcatcat catcacagca gcggccatat cgacgacgac 60
gacaagcata tgcaaattaa caattcctta aatagcttaa gtcaatatgt taaagtcaac 120
tcaaacgaag aaaatcaaaa ctctaaaaat caagaacaaa acgctttagc gcaagatcca 180
gctgtagagg taaatatcag caaagaagcc aaagaaaaat caaatacttc taatcaaaac 240
aattctcaag ctccagctca agctttaaac gcacaaaaca acacgcaaca agatagtagc 300
agcaatagtg aagataaact tacagaatta acacaaaagc ttgcagaaat tcaagcaaaa 360
attgttgaac taactgcgaa aatgtctaaa gctaatgagg atcaaatcaa aagtattgaa 420
agtcaaatag caacattaaa tgcccaagct tcaactattc aagctcaaat tcaagaactc 480
caaagccaac aagcttga 498

<210> SEQ ID NO 14
<211> LENGTH: 165
<212> TYPE: PRT
<213> ORGANISM: Campylobacter jejuni

<400> SEQUENCE: 14

Met Gly His His His His His His His His His His Ser Ser Gly His
1 5 10 15

Ile Asp Asp Asp Asp Lys His Met Gln Ile Asn Asn Ser Leu Asn Ser
20 25 30

Leu Ser Gln Tyr Val Lys Val Asn Ser Asn Glu Glu Asn Gln Asn Ser
35 40 45

Lys Asn Gln Glu Gln Asn Ala Leu Ala Gln Asp Pro Ala Val Glu Val
50 55 60

Asn Ile Ser Lys Glu Ala Lys Glu Lys Ser Asn Thr Ser Asn Gln Asn
65 70 75 80

Asn Ser Gln Ala Pro Ala Gln Ala Leu Asn Ala Gln Asn Asn Thr Gln
85 90 95

Gln Asp Ser Ser Ser Asn Ser Glu Asp Lys Leu Thr Glu Leu Thr Gln
100 105 110

Lys Leu Ala Glu Ile Gln Ala Lys Ile Val Glu Leu Thr Ala Lys Met
115 120 125

Ser Lys Ala Asn Glu Asp Gln Ile Lys Ser Ile Glu Ser Gln Ile Ala
130 135 140

Thr Leu Asn Ala Gln Ala Ser Thr Ile Gln Ala Gln Ile Gln Glu Leu
145 150 155 160

Gln Ser Gln Gln Ala
165

<210> SEQ ID NO 15
<211> LENGTH: 498
<212> TYPE: DNA
<213> ORGANISM: Campylobacter jejuni

<400> SEQUENCE: 15
atgggccatc atcatcatca tcatcatcat catcacagca gcggccatat cgacgacgac 60
gacaagcata tgaaaataga tactttgaca aaaaatttta gcaattatca aacacaaata 120
aacaaagaca atgatttggt aagtaatgtt catagcgaca atgtggttaa aattcaaatt 180
tcagatgaag caagaagttt aagtcaaaca aattcaaaaa atgaaaaaga atatgaaatc 240
aaagtaagtc aagaaaaaat agaaaaccac aaagaccaaa attccattca aaatagcaaa 300
ggtggcgtaa atcccgcatt agaggcttta atagcaaaat tagctgaaat tttagctaaa 360
attgcagaac ttactcaaaa aatgacaaac gctaacgaac aaatgaaaac gacatttcaa 420
aaacaaattg atgtgctaaa atctcaagca gatgtaattc aagctcaaat tcaagaactc 480
caaagccaac aagcttga 498

<210> SEQ ID NO 16
<211> LENGTH: 165
<212> TYPE: PRT
<213> ORGANISM: Campylobacter jejuni

<400> SEQUENCE: 16

Met Gly His His His His His His His His His His Ser Ser Gly His
1 5 10 15

Ile Asp Asp Asp Asp Lys His Met Lys Ile Asp Thr Leu Thr Lys Asn
20 25 30

Phe Ser Asn Tyr Gln Thr Gln Ile Asn Lys Asp Asn Asp Leu Val Ser
35 40 45

Asn Val His Ser Asp Asn Val Val Lys Ile Gln Ile Ser Asp Glu Ala
50 55 60

Arg Ser Leu Ser Gln Thr Asn Ser Lys Asn Glu Lys Glu Tyr Glu Ile
65 70 75 80

Lys Val Ser Gln Glu Lys Ile Glu Asn His Lys Asp Gln Asn Ser Ile
85 90 95

Gln Asn Ser Lys Gly Gly Val Asn Pro Ala Leu Glu Ala Leu Ile Ala
100 105 110

Lys Leu Ala Glu Ile Leu Ala Lys Ile Ala Glu Leu Thr Gln Lys Met
115 120 125

Thr Asn Ala Asn Glu Gln Met Lys Thr Thr Phe Gln Lys Gln Ile Asp
130 135 140

Val Leu Lys Ser Gln Ala Asp Val Ile Gln Ala Gln Ile Gln Glu Leu
145 150 155 160

Gln Ser Gln Gln Ala
165

<210> SEQ ID NO 17
<211> LENGTH: 1056
<212> TYPE: DNA
<213> ORGANISM: Campylobacter jejuni

<400> SEQUENCE: 17
atggccatca tacgttatat agctgacaag cacaacatgt tgggtggttg tccaaaagag 60
cgtgcagaga tttcaatgct tgaaggagcg gttttggata ttagatacgg tgtttcgaga 120
attgcatata gtaaagactt tgaaactctc aaagttgatt ttcttagcaa gctacctgaa 180

-continued

```
atgctgaaaa tgttcgaaga tcgtttatgt cataaaacat atttaaatgg tgatcatgta    240

acccatcctg acttcatgtt gtatgacgct cttgatgttg ttttatacat ggacccaatg    300

tgcctggatg cgttcccaaa attagtttgt tttaaaaaac gtattgaagc tatcccacaa    360

attgataagt acttgaaatc cagcaagtat atagcatggc ctttgcaggg ctggcaagcc    420

acgtttggtg gtggcgacca tcctccaaaa tcggatggtt caactagtgg ttctggtcat    480

caccatcacc atcactccgc gggtctggtg ccacgcggta gtactgcaat tggtatgaaa    540

gaaaccgctg ctgctaaatt cgaacgccag cacatggaca gcccagatct gggtaccggt    600

ggtggttctg gtgatgacga cgacaagatg caaattaaca attccttaaa tagcttaagt    660

caatatgtta aagtcaactc aaacgaagaa aatcaaaact ctaaaaatca agaacaaaac    720

gctttagcgc aagatccagc tgtagaggta aatatcagca aagaagccaa agaaaaatca    780

aatacttcta atcaaaacaa ttctcaagct ccagctcaag ctttaaacgc acaaaacaac    840

acgcaacaag atagtagcag caatagtgaa gataaactta cagaattaac acaaaagctt    900

gcagaaattc aagcaaaaat tgttgaacta actgcgaaaa tgtctaaagc taatgaggat    960

caaatcaaaa gtattgaaag tcaaatagca acattaaatg cccaagcttc aactattcaa   1020

gctcaaattc aagaactcca aagccaacaa gcttga                             1056
```

<210> SEQ ID NO 18
<211> LENGTH: 351
<212> TYPE: PRT
<213> ORGANISM: Campylobacter jejuni

<400> SEQUENCE: 18

```
Met Ala Ile Ile Arg Tyr Ile Ala Asp Lys His Asn Met Leu Gly Gly
1               5                   10                  15

Cys Pro Lys Glu Arg Ala Glu Ile Ser Met Leu Glu Gly Ala Val Leu
            20                  25                  30

Asp Ile Arg Tyr Gly Val Ser Arg Ile Ala Tyr Ser Lys Asp Phe Glu
        35                  40                  45

Thr Leu Lys Val Asp Phe Leu Ser Lys Leu Pro Glu Met Leu Lys Met
    50                  55                  60

Phe Glu Asp Arg Leu Cys His Lys Thr Tyr Leu Asn Gly Asp His Val
65                  70                  75                  80

Thr His Pro Asp Phe Met Leu Tyr Asp Ala Leu Asp Val Val Leu Tyr
                85                  90                  95

Met Asp Pro Met Cys Leu Asp Ala Phe Pro Lys Leu Val Cys Phe Lys
            100                 105                 110

Lys Arg Ile Glu Ala Ile Pro Gln Ile Asp Lys Tyr Leu Lys Ser Ser
        115                 120                 125

Lys Tyr Ile Ala Trp Pro Leu Gln Gly Trp Gln Ala Thr Phe Gly Gly
    130                 135                 140

Gly Asp His Pro Pro Lys Ser Asp Gly Ser Thr Ser Gly Ser Gly His
145                 150                 155                 160

His His His His His Ser Ala Gly Leu Val Pro Arg Gly Ser Thr Ala
                165                 170                 175

Ile Gly Met Lys Glu Thr Ala Ala Ala Lys Phe Glu Arg Gln His Met
            180                 185                 190

Asp Ser Pro Asp Leu Gly Thr Gly Gly Gly Ser Gly Asp Asp Asp Asp
        195                 200                 205

Lys Met Gln Ile Asn Asn Ser Leu Asn Ser Leu Ser Gln Tyr Val Lys
    210                 215                 220
```

-continued

```
Val Asn Ser Asn Glu Glu Asn Gln Asn Ser Lys Asn Gln Glu Gln Asn
225                 230                 235                 240

Ala Leu Ala Gln Asp Pro Ala Val Glu Val Asn Ile Ser Lys Glu Ala
                245                 250                 255

Lys Glu Lys Ser Asn Thr Ser Asn Gln Asn Asn Ser Gln Ala Pro Ala
            260                 265                 270

Gln Ala Leu Asn Ala Gln Asn Asn Thr Gln Gln Asp Ser Ser Ser Asn
        275                 280                 285

Ser Glu Asp Lys Leu Thr Glu Leu Thr Gln Lys Leu Ala Glu Ile Gln
    290                 295                 300

Ala Lys Ile Val Glu Leu Thr Ala Lys Met Ser Lys Ala Asn Glu Asp
305                 310                 315                 320

Gln Ile Lys Ser Ile Glu Ser Gln Ile Ala Thr Leu Asn Ala Gln Ala
                325                 330                 335

Ser Thr Ile Gln Ala Gln Ile Gln Glu Leu Gln Ser Gln Gln Ala
            340                 345                 350


<210> SEQ ID NO 19
<211> LENGTH: 37
<212> TYPE: DNA
<213> ORGANISM: Artificial Sequence
<220> FEATURE:
<223> OTHER INFORMATION: Primer DR103

<400> SEQUENCE: 19

ccatatgaaa atagatactt tgacaaaaaa ttttagc                              37
```

SECRETED *CAMPYLOBACTER* FLAGGELLA COREGULATED PROTEINS AS IMMUNOGENS

CROSS-REFERENCE TO RELATED APPLICATIONS

This application claims priority to U.S. Provisional application 60/800,099 filed May 12, 2006 and is a divisional application of U.S. patent application Ser. No. 11/800,955 filed May 8, 2007 (U.S. Pat. No. 8,221,764, issued on Jul. 17, 2012).

SEQUENCE LISTING

A written Sequence Listing is included in the Specification showing polypeptide and nucleotide sequences regarding secreted *Campylobacter jejuni* proteins.

BACKGROUND OF INVENTION

1. Field of the Invention

The invention relates to *Campylobacter jejuni* gene products and immunogenic fragments of the gene products useful as component(s) of a pharmaceutical formulation capable of eliciting an anti-*Campylobacter jejuni* immune response. The invention also relates to a method of using inducing an anti-Campylobacter immune response by the administration of *C. jejuni*-secreted, flagellar gene co-regulated gene products or immunogenic fragments of the gene products.

2. Description of the Related Art

*C. jejuni* is a leading cause of diarrheal disease worldwide and a documented threat to US military personnel (Taylor, 1992; Tauxe, 1992). The symptoms of *Campylobacter* enteritis include diarrhea, abdominal pain, and fever and often accompanied by vomiting. Stools usually contain mucus, fecal leukocytes and blood, although watery diarrhea is also observed (Cover and Blaser, 1999). However, despite the importance of this organism to human disease, there are no licensed vaccines against *C. jejuni.*

Although *Campylobacter* infection is treatable with antibiotics, an effective vaccine formulation against the organism is a preferred method for disease prevention. Vaccine administration is especially desirable for travelers to regions of the world where *Campylobacter* is endemic. However, there are currently no licensed vaccines for this organism. Further hampering efforts in anti-*Campylobacter* vaccine development is the potential initiation of Guillain-Barre Syndrome (GBS) individuals exposed to *Campylobacter* (Kuroki, et al, 1991). However, because of the importance of flagellin in *Campylobacter* virulence, these genes have been promising in the development of anti-*Campylobacter* immunity (U.S. Pat. No. 6,987,176 to Guerry, et al).

*Campylobacter* posses a single polar flagella that has been shown to be critical for intestinal colonization and invasion (Wassennar, et al, 1991; Yao, et al, 1994). Flagellin has been shown to be the immunodominant antigen during human and animal infection and is required for colonization in vivo (Guerry, et al, 2000). Flagellar biosynthesis is regulated in a hierarchical fashion with genes expressed in the order in which they are required for the assembly of the flagellum. The production of flagella, however, requires significant expenditure of energy. Therefore, the regulation of these genes is of critical importance to the organism. However, unlike other bacterial species, only three sigma factors have been identified *Campylobacter jejuni* ($\sigma^{70}$, $\sigma^{54}$ and $\sigma^{28}$) (Parkhill, et al, 2000). These observations suggested that a number of *Campylobacter* genes are coordinately regulated.

Among members of the family Enterobacteriaceae, the genes flhC and flhD are the initial regulators of the flagellar regulatory cascade (Macnab, 2003). Within this scheme, a feedback mechanism ensures the correct order of flagellar gene expression. In *Campylobacter jejuni*, which lacks the flhC and flhD regulators, the genes in the flagella regulon expressed intermediate and late in the flagella regulatory cascade are controlled by the sigma factors $\sigma^{54}$ and $\sigma^{28}$, respectively.

Based on studies using the flhA gene and the gene fliA in the *C. jejuni* strain NCTC 11168, it has been observed that some genes of unknown functions, but not appearing to be directly involved in flagella function, were also co-regulated along with those genes associated with flagella function (Parkhill, et al, 2000); Carillo, et al, 2004). The flhA gene is expressed early in the cascade and which is involved in export of flagella proteins and the gene fliA encodes $\sigma^{28}$. Later studies have shown that many of these genes are also down-regulated in flagella mutants in *C. jejuni* 81-176, including the gene Cj0977 (Goon, et al, 2006).

The Cj0977 proteins, which are co-regulated with the flagella regulon, are 21.2 kDa and are 98% identical between the *C. jejuni* strains NCTC 11168 and 81-176 (Goon, et al, 2006). Furthermore, using a Cj0977 mutant, it was shown that Cj0977 resulted in significant attenuation of disease, using the ferret diarrhea disease model. However, the role of Cj0977 in virulence is still not understood. Furthermore, although Cj0977 is clearly important for virulence (Goon, et al, 2006), the protein has not been found to be secreted.

A putative $\sigma^{28}$-regulated gene, Cj0859c, encodes a protein with no homology to known proteins, and maps in a region of the chromosome that has been reported in a recent micrarray study to be variable among strains (Parker, et al, 2006). Reduced expression of this gene has been shown in a fliA mutant of NCTC 11168 (Carillo, et al, 2004). Analysis of this region in the *C. jejuni* genomes indicated that the putative $\sigma^{28}$ promoter was conserved, but that there was variation in the Cj0859c gene.

There is currently no effective anti-*Campylobacter* vaccine. Therefore, the identification of new anti-*Campylobacter* immunogenic formulations is of critical importance.

SUMMARY OF INVENTION

An aspect of this invention is a composition with homology to the *Campylobacter jejuni* protein Cj0859c that is normally co-regulated with *C. jejuni* flagellar proteins. The inventive composition can be isolated and prepared from natural *C. jejuni* isolates or be recombinantly produced. Included in the inventive composition are alternative forms of the same protein.

Another aspect of this invention is a method of inducing an immune response against *Campylobacter* by the administration of Cj0859c.

DESCRIPTION OF THE PREFERRED EMBODIMENTS

Figure 1:
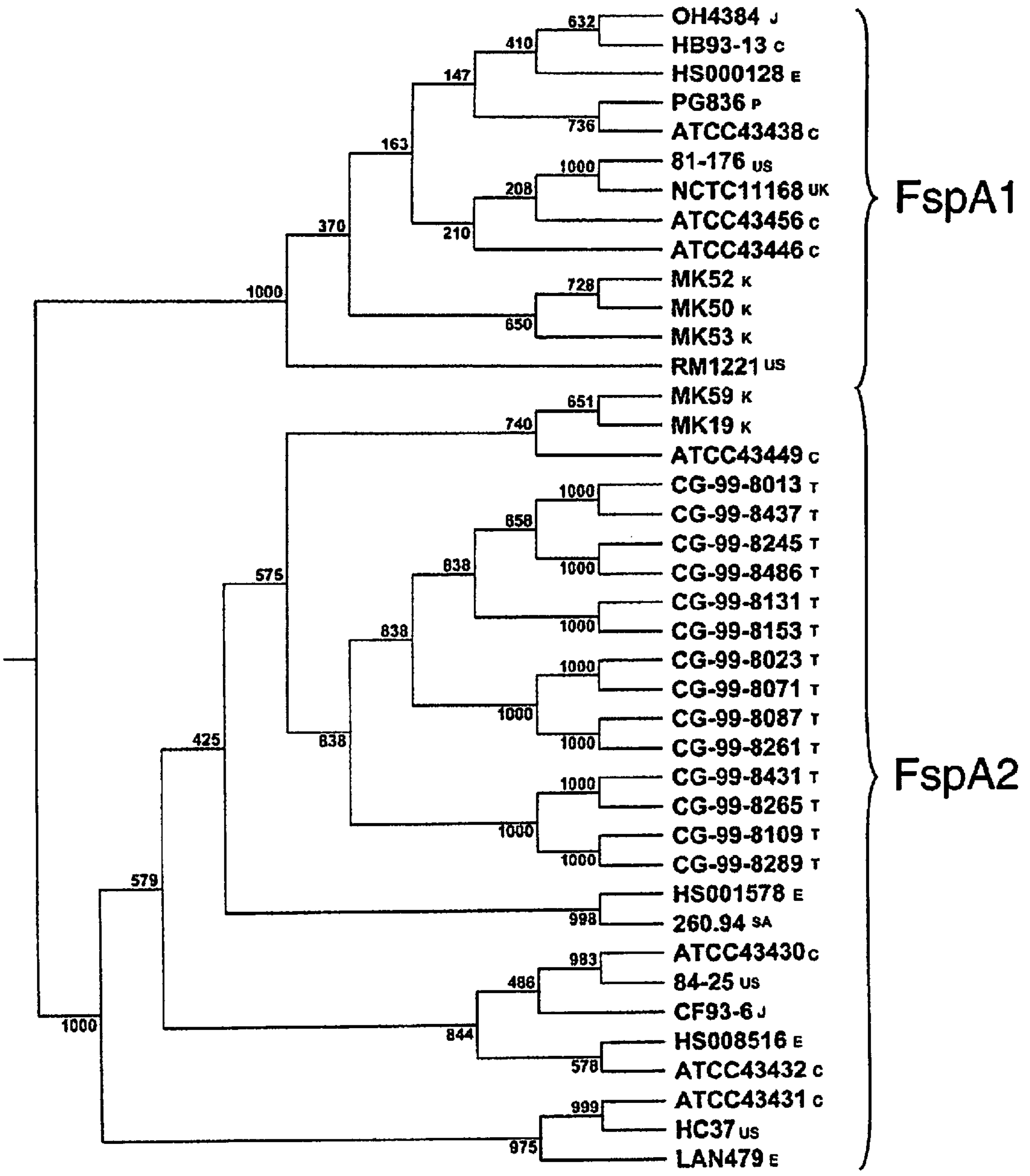
FIG. 1. Phylogenetic tree based on protein sequences encoded by alleles of the fspA gene.

It has been observed that a number of *Campylobacter jejuni* genes of unknown function are nonetheless co-regulated with flagellar gene expression. These include the genes: Cj0859c (both A1 and A2 forms); Cj0243c; Cj1476; Cj1467; Cj1650; Cj1450; Cj1656c; Cj0391c. FlaC is secreted by not co-regulated with flagellar gene expression. Because of the importance of these genes in the pathogenesis of *Campylobacter jejuni*, flagella co-regulated genes that encode polypeptides that are secreted and are therefore accessible to the host immune response may be important immunologically. Therefore, an aspect of this invention is the use of these gene products in the development of anti-*Campylobacter jejuni* formulations.

Microarray analysis was conducted on these genes in order to ascertain the coordinate expression of these *C. jejuni* genes. The microarray assay contained PCR amplicons representing 1503 *C. jejuni* open reading frames. Most genes were sequenced using DNA from the *C. jejuni* strain NCTC 11168 (Parkhill, et al, 2000) or the strain 81-176. All predicted flagellin genes were included except flgI (Cj1462), flgA (Cj0769c) and flgM (Cj(1464). The result of this analysis is illustrated in Table 1.

In Table 1, bioinformatic analysis of the scanned arrays was performed using Microarray Suite version 5.1™ (Affymetrix). Duplicate microarray hybridizations were done on two independent preparations of RNA from each strain. The mean and standard deviations for the mutants in the flagella genes was calculated from the four microarray experiments. A change in signal was considered differentially regulated if the statistically significant change in expression was greater than 1.5-fold. The results are expressed as the fold difference in expression of the mutant compared to the wildtype in $\log_2$. Thus, a sample reported as "−2" is a four-fold reduction in the mRNA levels in the mutant compared to wildtype; "−3" indicates an eight-fold reduction. The genes listed in Table 1 are not required for flagella biogenesis but were nonetheless 2 to greater than 250-fold down-regulated in strains with mutation in genes known to be involved in flagella biogenesis indicating their co-regulation with flagellar genes indicating their flagellar co-regulation. The characteristics of one of the genes listed in Table 1, Cj0977, was previously described (Goon, et al, 2006).

The data in Table 1 indicates that the genes Cj0859c; Cj0391; Cj1450; Cj1650; Cj 1656c; Cj0243c; Cj 1476; Cj 1728c; Cj0040 are co-regulated with flagellar genes. The data illustrated in Table 1 is consistent with the notion that Cj0859c is under the control of $\sigma^{28}$ since there is reduced gene expression (i.e., RNA) detected in fliA ($\sigma^{28}$) mutant because of feedback in the flagella regulon. Additionally, it has been previously shown that FlaC is secreted through the flagella filament (Song, et al, 2004) but it has not been previously shown to show any co-regulation with flagella.

TABLE 1

| | Promoter | flgR | flgS | rpoN | fliA | flgA |
|---|---|---|---|---|---|---|
| Cj0045c | | −3.8 | −0.7 | −2.9 | −4.7 | −1.1 |
| C1025c | | −2.1 | −2.4 | −1.7 | 0.3 | 0.5 |
| Cj1034c | | −1.8 | −2.6 | −1.7 | −2.3 | −0.8 |
| Cj0040 | $\sigma^{54}$ | −7.5 | −0.1 | −8.7 | 1.8 | 0.5 |
| Cj0243c | $\sigma^{54}$ | −4.2 | −2.6 | −5.8 | 1.4 | −0.1 |
| CjB0814 | $\sigma^{54}$ | −4.4 | −3.5 | −3.4 | 1.7 | 0.7 |
| Cj1467 | $\sigma^{54}$ | −2.6 | −1.6 | −2.4 | 0.5 | 0.7 |
| Cj1650 | $\sigma^{54}$ | −5.7 | −4.5 | −5.5 | 1 | 0.7 |
| Cj1728c | $\sigma^{54}$ | −4.8 | 0.1 | −3.9 | 2.2 | 1.4 |
| Cj0977 | $\sigma^{28}$ | −2.7 | −3.7 | −2.1 | −4.2 | −0.4 |
| Cj0859c | $\sigma^{28}$ | −2.7 | −3.8 | −2.9 | −5.4 | −1 |
| Cj1450 | $\sigma^{28}$ | −1.2 | −2.1 | −0.5 | −1.5 | −0.8 |
| Cj1656c | $\sigma^{28}$ | −0.6 | −2.8 | −1.1 | −7.5 | −0.4 |
| Cj0391 | $\sigma^{28}$ | −0.2 | −1.2 | −1.2 | −2 | −0.7 |
| Cj0720/flaC | | 0.2 | −1.3 | −0.1 | 0.2 | −1.6 |

Also illustrated in Table 1, the genes Cj0040 and Cj0977 are not known to be secreted and therefore are not suitable as immunogenic candidates. Additionally, Cj 1728c is likely an inner membrane protein and is therefore also not likely to be able to be highly immunogenic. However, the proteins Cj0391; Cj 1450; Cj 1650; Cj0243c and Cj1476, like Cj0859c, are co-regulated with flagellar genes as well as likely to be secreted from the bacteria. Further analysis of Cj0859c revealed this moiety to be an important candidate against *Campylobacter*. The gene encoding Cj0859c has been termed "flagella secreted protein A" (fspA).

EXAMPLE 1

Characterization of Fsp

Characterization of the gene locus was conducted by DNA sequence analysis of PCR products derived from a collection of isolates. The variation of fspA by DNA sequence analysis of polymerase chain reaction (PCR) products generated from a collection of isolates from diverse geographical locations is illustrated in FIG. 1. In obtaining the data illustrated in FIG. 1, The Cj0859c-Cj0860 region of the chromosome of *C. jejuni* strains was PCR amplified using primers pg06.14 (SEQ ID. No. 5) and pg06.15 (SEQ ID. No. 6). Primer pg06.14 bound to the pabA gene (Cj0861) and pg06.15 bound to murA (Cj0858c). Amplicons were subjected to DNA sequence analysis using Big Dye Chemistry on an Applied Biosystems Model 3100 DNA™ sequencer and the sequences were assembled using Sequencher 4.5™ (Gene Codes). Each consensus sequence was manually inspected for quality assessment of the assembly. The Cj0859c gene sequence was identified and the biological sequences compared using commercially available software.

As shown in FIG. 1, two overall clusters of Cj0859c alleles are evident. The FspA1 cluster, which included 81-176, NCTC 11168 and RM1221, comprised 32% of the total strains (13/41). The FspA2 cluster comprised 68% of the total strains (28/41). The FspA2 cluster includes TGH9011, which was originally reported to lack Cj0859c based on micro array analysis using the NCTC 11168 allele as probe (36). The allele found in TGH9011, however, is truncated (i.e., is not detectable by immunoblot). The FspA1 proteins share a minimum of 81.7% identity within the group, and the FspA2 proteins share a minimum of 95.1% identity. There appeared to be no association of allele type and geographical isolation, although all of the Thai isolates examined contained the FspA2 allele.

EXAMPLE 2

Production of FspA Construct

Construction of GST-his-Fsp $A_{81176}$ was conducted by was amplifying the fspA81176 gene from 81-176 by polymerase chain reaction (PCR). The template was DNA from strain 81-176 and the primers were: pg05.53 (SEQ ID. No. 7) and pg05.54 (SEQ ID. No. 8). These primers included sequences for cloning into pET41-EK LIC™, a vector that allows fusion to both a GST tag and hexahistidine tag (EMD Bioscience, Madison, Wis.). The 429 bp amplicon was purified using Qiaquick™ PCR purification columns (Qiagen, Valencia, Calif.) and ligated to pET41-EK LIC as directed by the manufacturer, and transformed into NovaBlue™ GigaSingles™ cells (EMD Biosciences). Several resulting clones were sequenced and one, which showed the predicted sequence, was selected for protein purification. The GST-his-Cj0859c protein (SEQ ID No. 18) was purified by nickel chromatography. The nucleic acid sequence encoding the GST-his-Cj0859c polypeptide is SEQ ID No. 17.

The FspA protein from 81-176 was also expressed as a histidine-tagged protein in *E. coli* for biological experiments as follows. The gene was PCR amplified from 81-176 using primers DR101 (5'-CCATATGCAAATTAACAATTCCTTAAATAGC-3') and DR102 (5'-GGGATCCTCAAGCTTTGTTGGCTTTGGAGTTC-3') and HF2 DNA polymerase (Clontech, Mountain View, Calif.). The resulting amplicon was digested with NdeI and BamHI and cloned into NdeI-BamHI-digested pET-19b (Novagen, San Diego, Calif.) in *E. coli* DH5α. The amino acid sequence of the histidine-tagged FspA1 (i.e., 81-176) is SEQ ID. No. 14, which is encoded by the nucleic acid sequence of SEQ ID No. 13.

FspA from CG8486 was expressed as a histidine-tagged protein in pET-19b using primers DR103 (5'-CCATATGAAAATAGATACTTTGACAAAAAATTTTAGC-3') and DR102 (shown above), as described above for 81-176. The amino acid sequence of the histidine tagged FspA2 (i.e., CG8486) is SEQ ID. No. 16, which is encoded by the nucleic acid sequence of SEQ ID No. 15.

A mutant in $fspA_{81176}$ was constructed using a Tn5 based in vitro transposition with a cat cassette as previously described (18). The in vitro reaction was performed according to manufacturer's instructions with a clone from a Sau3A1 partially digested ordered genomic library of 81-176 called pLCH8-63 as the target DNA. This clone contained the region of the 81-176 chromosome that corresponded to genes Cj0856c-Cj0860.

The reaction products were transformed into *E. coli* DH5α and plasmid DNAs from individual transformants were sequenced using primers that read out from within the cat cassette to determine the insertion point and the orientation of the transposon within the gene. A plasmid was selected in which the cat cassette had inserted 259 bp from the translational start of fspA in the same orientation as fspA. This plasmid was used to electroporate *C. jejuni* 81-176 with selection on Muller Hinton agar supplemented with chloramphenicol (15 μg/ml). The successful mutation of fspA was verified by PCR with primers bracketing the $Cm^r$ insertion point to confirm that the DNA had undergone a double cross-over. This mutant was called PG2572.

EXAMPLE 3

Secretion of Cj0859c

The ability of the Cj0859c (FspA) to be secreted was demonstrated. This study was conducted by western blot analysis using whole cells of *C. jejuni* 81-176 as a source of antigen as well as an isogenic insertional mutant of $fspA_{81176}$. The blots were probed with rabbit polyclonal antiserum against a recombinant form of the protein (GST-his-$FspA_{81176}$). See Example 2 for production of GST-his-$FspA_{81176}$.

Figure 2:
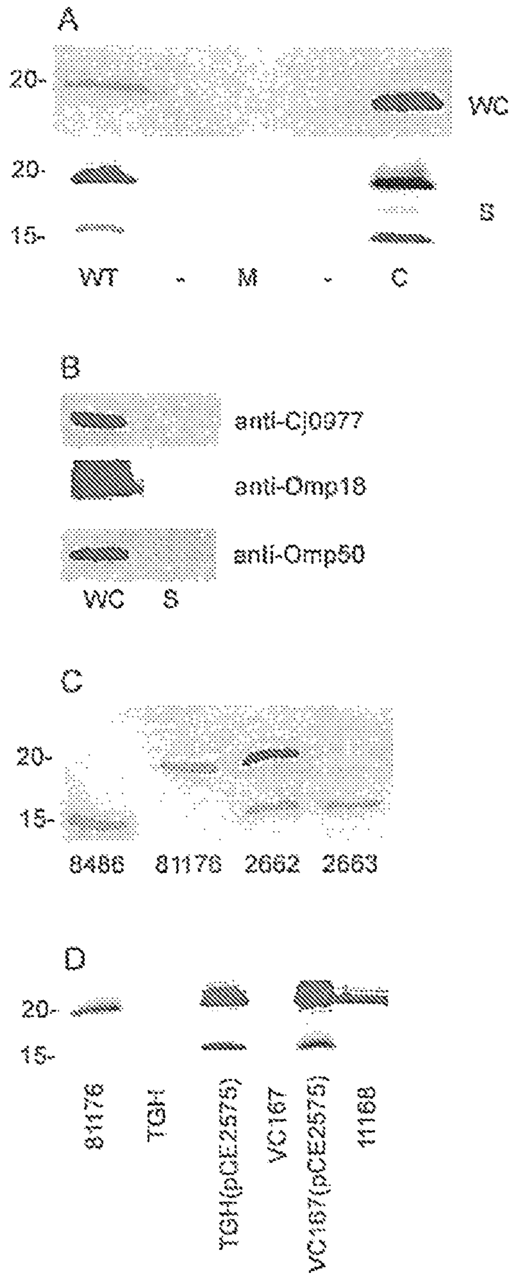
FIG. 2. Secretion of FspA.

As illustrated in FIG. 2, the presence of a band in wildtype 81-176 with an apparent $M_r$ of approximately 18 kDa, slightly larger than the predicted $M_r$ of $FspA_{81176}$. A histidine-tagged version of this protein expressed in *E. coli* also migrated aberrantly in SDS-PAGE (data not shown). This band was missing in the $fspA_{81176}$ mutant and appeared to be over expressed when the mutation was complemented in trans. Since *C. jejuni* is known to secrete multiple proteins through flagella, we examined supernatants for the presence of Cj0859c.

$FspA_{81176}$ was found in supernatants of 81-176 cultures and the complement of the mutant, but not in supernatants of the fspA mutant (FIG. 2A). Additional cross-reacting bands were also observed in some supernatant preparations and may represent processing events, degradation products, or cross-reacting proteins. To control for possible cell leakage, whole cell and supernatant preparations of 81-176 were immunoblotted with antibodies to recombinant forms of three other proteins, as shown in FIG. 2B. These were Cj0977, another $\sigma^{28}$-regulated cytoplasmic protein that is not secreted (Goon, et al, 2006), Omp18, a lipoprotein (Burnens, et al, 1995) and Omp50, an outer membrane protein (Bolla, et al, 2000). These proteins were readily detected in whole cells, but not in the supernatant preparations.

It was further determined that the $FspA_{8486}$ protein is secreted from 81-176 when the gene is supplied in trans (see Example 2). In these studies, the fspA gene and its $\sigma^{28}$ promoter were PCR amplified from 81-176 using the following primers: pg05.133 (SEQ ID. No. 11) and pg05.134 (SEQ ID. No. 12. These primers added BamHI and EcoR1 sites, respectively. The resulting 744 bp amplicon was digested with BamHI and EcoRI (New England Biolabs, Beverly, Mass.) and cloned into similarly digested pRY107 (50). After confirmation that the clone was correct by DNA sequence analysis, the plasmid was transformed into DH5α cells carrying RK212.2. The resulting cells were used as donors to transfer conjugatively the complementing plasmid, pCE2575, into PG2166, the Cj0859c mutant, with selection on kanamycin and chloramphenicol.

It was observed that the $FspA_{8486}$ protein can also found in the supernatant of cultures of CG8486, as shown in FIG. 2C, but did not show the aberrant migration observed with $FspA_{81176}$. The fspA gene and its $\sigma^{28}$ promoter from CG8486 were inserted into the astA gene of 81-176 to generate PG2662. The two forms of FspA can be visualized in the supernatant of this strain by immunodetection with anti-$FspA_{8486}$ antiserum (FIG. 2C). Only $FspA_{8486}$ can be visualized in the supernatant of strain PG2663, the $fspA_{81176}$ mutant of 81-176 containing $fspA_{8486}$ inserted into astA. Cj0859c or fspA has been reported to be missing in several strains of *C. jejuni* by micro array analysis, including ATCC 43431 (TGH9011)(see Parker, et al, 2006; Poly, et al, 2005 and Poly et al, 2004). The gene was also absent in the sequenced strains of *Campylobacter coli, Campylobacter upsaliensis, Campylobacter lari*, and *Helicobacter* spp. Cj0859c was not detectable in whole cell immunoblots (data not shown) or supernatants of either *C. jejuni* TGH9011 or a *C. coli* strain, VC167 T2 (FIG. 2D). However, when pCE2575 carrying $fspA_{81176}$ was transferred conjugatively into these strains, $FspA_{81176}$ protein could readily be detected in both whole cells (data not shown) and in cell supernatants (FIG. 2D) indicating that the requisite machinery was present in these other *Campylobacter* strains to secrete the $FspA_{81176}$ protein. Doublets of the $FspA_{81176}$ protein were also observed in supernatants from these strains, as seen in FIG. 3D.

Figure 3:
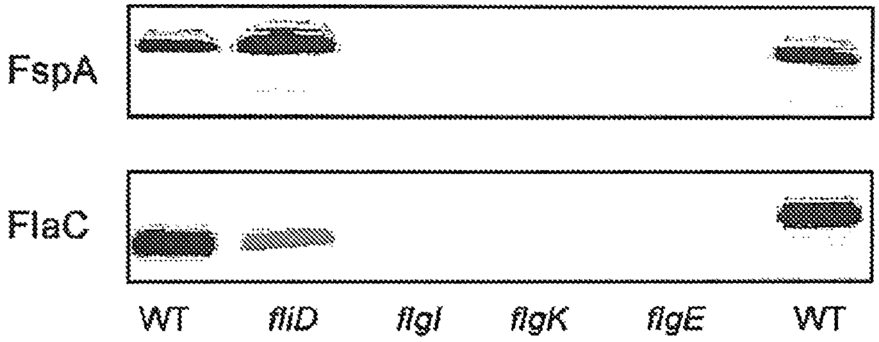
FIG. 3. Illustration of requirement for minimum flagella structure for secretion of FspA.

Song et al. (41) showed that FlaC secretion to the supernatants was not observed in *C. jejuni* TGH9011 mutants lacking hook (flgE) and basal body structures (flgF). We further examined secretion of $FspA_{81176}$ from similar mutants, as shown in FIG. 3. The results indicate that neither $FspA_{81176}$ nor FlaC was secreted in 81-176 mutants in flgE, flgI, encoding the P ring subunit, or flgK, encoding the hook-filament junction protein. Both proteins were secreted from a mutant in fliD lacking the filament cap protein. Therefore, secretion of $FspA_{81176}$ requires a minimum flagella structure.

EXAMPLE 4

The Role of Cj0859c in Bacterial Virulence

Mutation of $fspA_{81176}$ does not affect 81-176 adherence or invasion of INT407 cells. There was no significant difference between wildtype 81-176 and an fspA::cat mutant, which was fully motile, in terms of adherence (P=0.56) to or invasion of INT407 cells (P=0.61).

Figure 4:
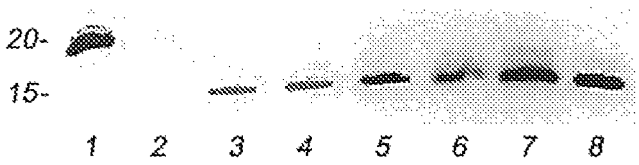
FIG. 4. Interaction of FspA proteins with INT407 cells.

Recombinant his-tagged $FspA_{8486}$ and $FspA_{81-176}$ proteins were added to a monolayer of INT407, incubated for 2 h, and washed extensively. The monolayer was lysed and the proteins separated in 12% SDS-PAGE gels and immunodetected. The results, shown in FIG. 4. In FIG. 4, Hexahistidine-tagged recombinant FspA1 or FspA2 (SEQ ID No. 14 and 16, respectively) were added to a monolayer of INT407 cells, which were then incubated for 4 hours at 37° C. After washing, an aliquot of a lysate was electrophoresed on a 12.5% SDS-PAGE gel, transferred to a nitrocellulose membrane and probed with anti-histidine-tagged mouse monoclonal antibody. In FIG. 4, Lane 1 shows recombinant FspA1; lane 2, INT407 cells plus 50 µg FspA1; lane 3, INT407 cells plus 5 µg FspA2; lane 4, INT407 cells plus 10 µFspA2; lane 5, INT407 cells plus 25 µg FpA2; lane 6, INT407 cells plus 50 µg FspA2; lane 7, recombinant FspA2; lane 8, recombinant FspA2. The results illustrated in FIG. 4, indicated that $FspA_{8486}$ remained associated with the monolayer, while $FspA_{81176}$ could not be detected in the lysate. These results illustrate that $FspA_{8486}$, but not $FspA_{81176}$, binds to INT407 cells.

Figure 5:
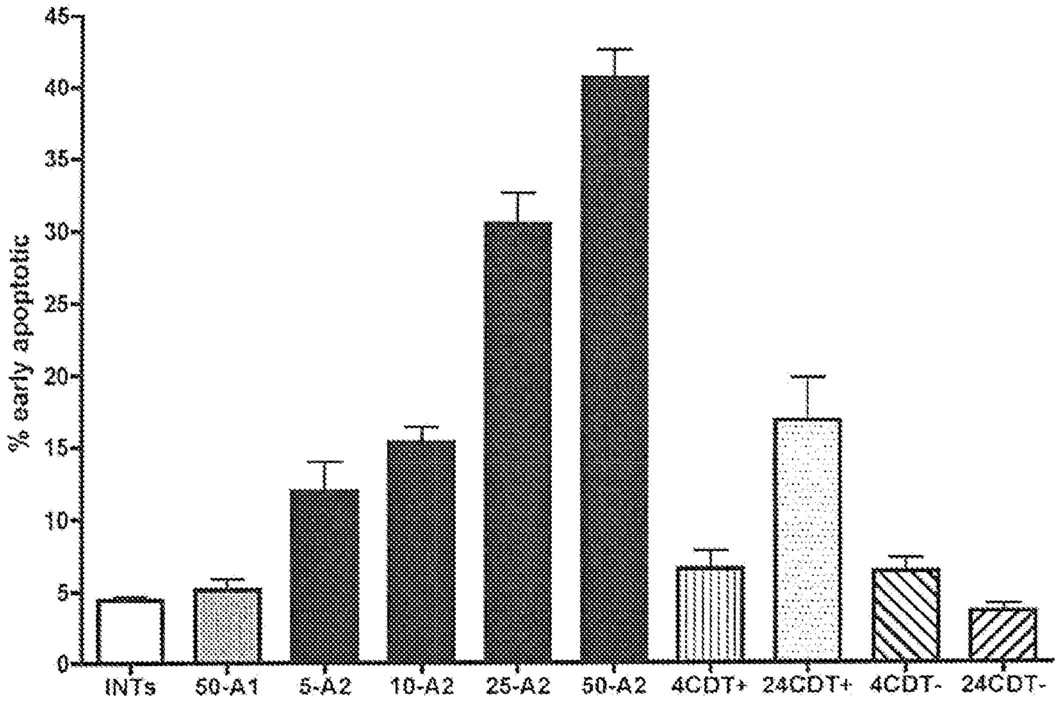
FIG. 5. Apoptosis induction by FspA2.

Additionally, $FspA_{8486}$ but not $FspA_{81176}$ causes induction of apoptosis of INT407 cells. Recombinant his-tagged $FspA_{8486}$ protein, but not recombinant his-tagged $FspA_{81176}$ protein, caused induction of apoptosis in INT407 cells after 4 h incubation, as shown in FIG. 5. Moreover, there was a clear dose response to the recombinant $FspA_{8486}$ protein. Addition of 5 µg of recombinant $FspA_{8486}$ resulted in 11.9%±4.7% of the cells in early apoptotic stage (P=<0.05 compared to untreated INT407 controls). Addition of increasing amounts of $FspA_{8486}$ from 10 µg to 50 µg resulted in a range of 15.4±2.4% to 30.9±4.8% of the cells in early apoptosis by 4 h (P<0.001). In contrast, addition of 50 µg of $FspA_{81176}$ to the monolayer showed no differences compared to untreated controls. The kinetics of induction of apoptosis was markedly quicker than that caused by CDT (Cortes-Bratti, et al, 2001; Gelfanova, et al, 1999; and Hickey, et al, 2005). Membrane preparations (a total of 10 µg total protein) from 81-176 (CDT+) caused apoptosis in only 6.6±3.0% of the cells in 4 h and 17±8% by 24 h. Membranes from a cdtA mutant of 81-176 had no effect, as previously reported (Hickey, et al, 2000; Hickey, et al, 2005).

EXAMPLE 5

Immunogenicity of FspA1 and FspA2

A murine study were undertaken in order to evaluate the immunogenicity and potential protective efficacy of the inventive anti-FspA constructs. In the study, adult female BALB/c mice were lightly anesthetized with isoflurane and immunized intranasally with 30 µl of PBS containing the FspA1 or FspA2 protein alone or a mucosal adjuvant LTR192G. The experimental groups are illustrated in Tables 2 and 3.

TABLE 2

| Experimental groups for FspA1 | | | |
|---|---|---|---|
| Group | FSPA1 (µg) | LTR192G (µg) | N |
| 1 | 0 | − | 10 |
| 2 | 5 | − | 9 |
| 3 | 5 | + | 10 |
| 4 | 25 | − | 10 |
| 5 | 25 | + | 10 |
| 6 | 100 | − | 10 |
| 7 | 100 | + | 9 |

TABLE 3

| Experimental groups for FspA2 | | | |
|---|---|---|---|
| Group | FSPA1 (µg) | LTR192G (µg) | N |
| 1 | 0 | − | 8 |
| 2 | 5 | − | nd |
| 3 | 5 | + | 8 |
| 4 | 25 | − | 8 |
| 5 | 25 | + | 8 |
| 6 | 100 | − | 8 |
| 7 | 100 | + | 8 |

Figure 6:
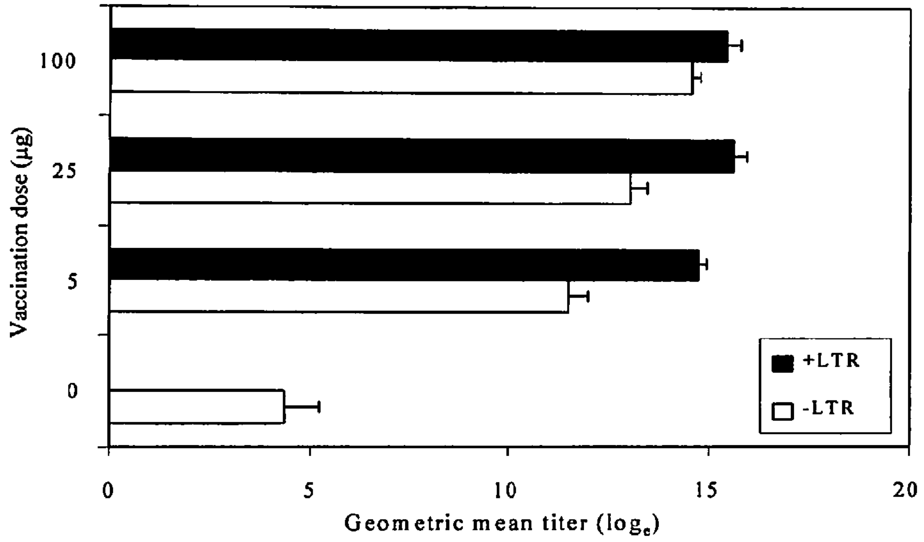
FIG. 6. Illustration of IgG and IgA response to FspA1
Figure 6:
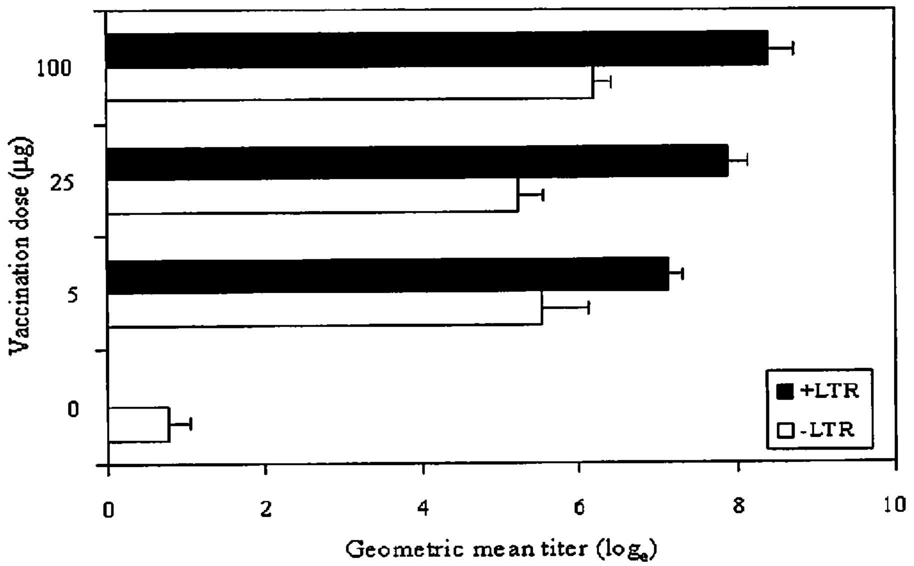
Figure 7:
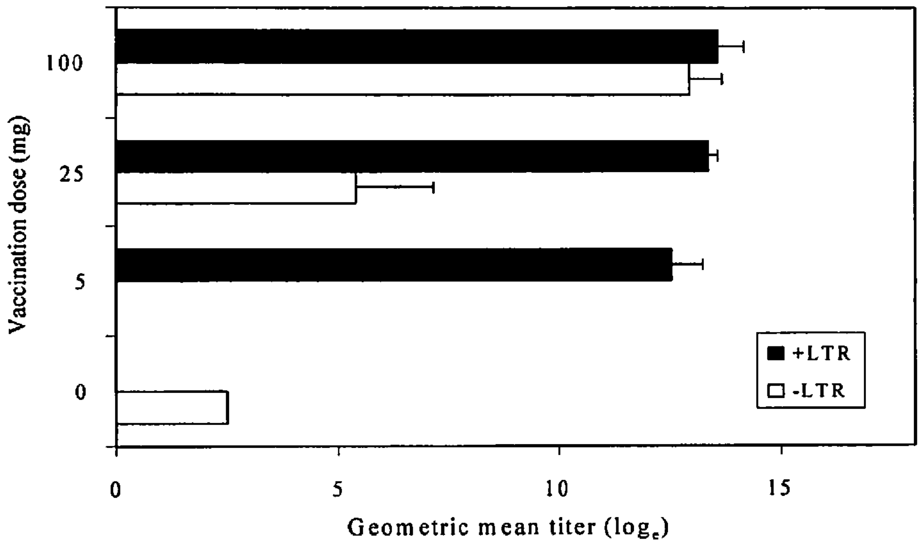
FIG. 7. Illustration of IgG and IgA response to FspA2.
Figure 7:
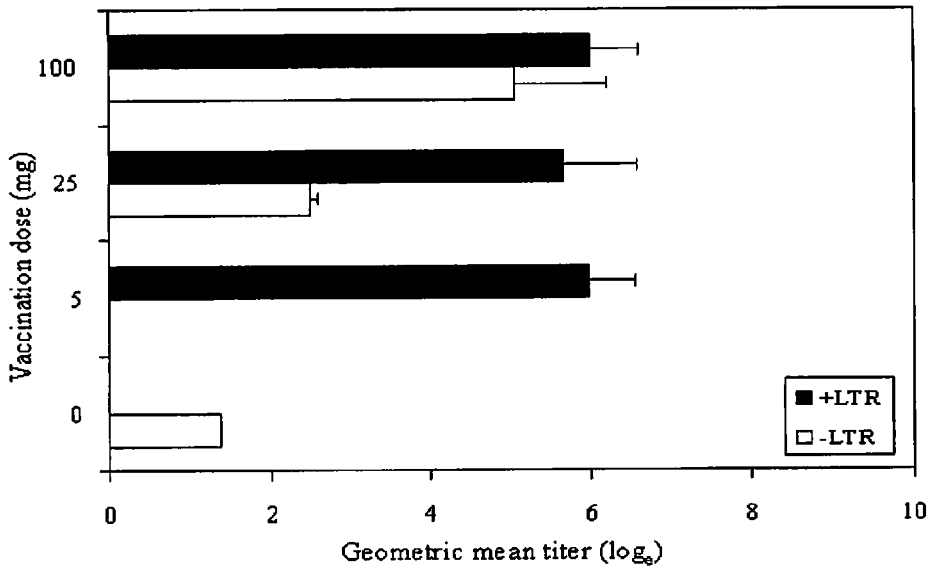

Three doses of vaccine were delivered at 14-day intervals (study days 0, 14 and 28). Seven (7) days after the last vaccination (study day 35) fecal pellets were collected to determine secretory IgA. Antigen-specific serum IgG was determined in tail blood that was collected 21-22 days (study day 49-50) after last vaccination. ELISA determined antigen-specific responses. The IgG and IgA responses are illustrated in FIG. 6 for mice immunized with FspA1 and FIG. 7 for mice immunized with FspA2. The data presented in FIGS. 6 and 7 are presented as group geometric mean titer (natural $\log_e$) and standard deviation.

All animals were challenged (study day 58) intranasally with $3\times10^9$ du of *C. jejuni* 81-176 for mice immunized with FSPA1 or *C. jejuni* CG8486 for mice immunized with FSPA2. Following challenge, animals were followed for 6 consecutive days for the development of the infection-associated illness. Based on the severity of sickness a score was assigned to each animal as follows:

0=No apparent illness
1=ruffled fur
2=ruffled fur and hunched back
3=dead

A daily sickness index, and then group average indices were determined and vaccine efficacy was calculated as: (Control−vaccinated)/(Control)×100. Efficacy is represented in Table 4, for mice immunized with FspA1, and in Table 5, for mice immunized with FspA2.

As illustrated in FIG. 6A, FspA1 induced a robust vaccine dose dependent serum IgG response. This response was further enhanced by inclusion of a mucosal adjuvant LTR192G. Animals immunized with PBS showed only low levels of anti-FSPA1 IgG responses (mean+2 standard deviations=<1:500). Based on this cut off, all animals in all groups were categorized as IgG responders.

Similar to serum IgG, a robust mucosal IgA response was detected after vaccination (see FIG. 6B). Interestingly, LTR192G had a greater adjuvant effect on mucosal IgA response than observed for IgG. Animals immunized with PBS showed no detectable levels anti-FSPA1 fecal IgA responses (mean+2 standard deviations=<1:4). Based on this cut off, all animals in all groups were categorized as sIgA responders.

As illustrated in Table 4, FspA1 exhibited significant protective efficacy against *C. jejuni* challenge. As shown in Table 4, even without adjuvant, over 50% efficacy was observed, with co-administration of adjuvant enhancing the protective efficacy further.

TABLE 4

FspA1 efficacy in mice challenged with *C. jejuni* 81-176

| Group | FSPA1 (μg) | LTR192G (μg) | Illness index (mean ± sd) | Efficacy ((%) |
|---|---|---|---|---|
| 1 | 0 | − | 1.14 ± 0.22 | n/a |
| 2 | 5 | − | 0.94 ± 0.21 | 17 |
| 3 | 5 | + | 0.78 ± 0.20 | 31 |
| 4 | 25 | − | 0.59 ± 0.56 | 48 |
| 5 | 25 | + | 0.38 ± 0.17 | 67 |
| 6 | 100 | − | 0.47 ± 0.13 | 59 |
| 7 | 100 | + | 0.32 ± 0.16 | 71 |

As illustrated in FIG. 7, animals immunized with FspA2 exhibited a dose dependent serum IgG response (FIG. 7A), with administration of 25 μg of vaccine alone inducing a low level IgG response (50% responders). Conversely, 100 μg induced a potent IgG repose in all animals. Animals immunized with PBS alone showed only low levels of anti-FspA2 IgG responses (mean+2 standard deviations=<1:100). Administration of FspA2 with LTR192G a robust IgG response, even at the 5 μg dose.

Referring to FIG. 7B, only 100 μg dose was able to induce mucosal IgA when delivered alone. As observed for IgG responses, co-delivery of vaccine with LTR192 resulted in equivalent levels of antigen-specific sIgA, even down to the 5 μg dose. Animals immunized with PBS showed no detectable levels anti-FSPA2 fecal IgA responses (mean+2 standard deviations=<1:4). The adjuvant effect, in these studies, was more pronounced in the mucosal IgA response than in the serum IgG response.

Animals immunized with 5 μg of FspA2 showed only minimal protection, as illustrated in Table 5. However, moderate protection was evident at higher doses with the adjuvant LTR192G providing some enhancement of protection.

TABLE 5

FspA2 efficacy in mice challenged with *C. jejuni* 8486

| Group | FSPA1 (μg) | LTR192G (μg) | Illness index (mean ± sd) | Efficacy ((%) |
|---|---|---|---|---|
| 1 | 0 | − | 1.23 ± 0.25 | n/a |
| 2 | 5 | − | nd | |
| 3 | 5 | + | 1.06 ± 0.34 | 13.8 |
| 4 | 25 | − | 1.05 ± 0.27 | 14.6 |
| 5 | 25 | + | 0.79 ± 0.31 | 35.8 |
| 6 | 100 | − | 0.77 ± 0.20 | 37.4 |
| 7 | 100 | + | 0.64 ± 0.21 | 47.9 |

These studies illustrate the utility of these constructs as components, alone or in combination with other moieties, of vaccines against *Campylobacter*. Accordingly, the inventive constructs can be used in methods for the induction of protective anti-*Campylobacter* immunity.

A prophetic method for the induction of the anti-*C. jejuni* mediated response in humans contains the following steps:

a. administration of immunogen comprising FspA1 or FspA2, or immunogenic fragments, thereof, with or without a tag, such as histidine or GST. If a boosting dose or doses are to be given this first administration of immunogen is a priming dose. The immunogen can be derived from isolated native polypeptide or recombinantly produced FspA, or FspA fragments. The immunogen can be administered orally, nasally, subcutaneously, intradermally, transdermally, transcutaneously intramuscularly, or rectally. The range of a unit dose of immunogen is 50 μg to 1 mg of immunogen. The immunogen is administered in any number of aqueous buffered solutions with or without carrier protein or adjuvant. The adjuvant can be any number of potential adjuvants, including LTR 192G.

b. The inventive method also contemplates immunization with or without administration of subsequent boosting. The boosting step comprises the administration of, subsequent to a priming dose, 1 to 4 boosting doses with a unit dose range of 50 μg to 1 mg of immunogen in a buffered aqueous solutions.

Alternative embodiments of the inventive method include inserting nucleotide constructs encoding FspA1 or FspA2, or fragments thereof, into an expression system capable of expression in mammalian subjects. In this embodiment, the expression system can be a viral or DNA expression vector. Another alternative embodiment of the inventive method is to induce immunity by administering a live attenuated carrier strain of bacteria transformed with a suitable viral or DNA expression system that contains one or more nucleic acid sequences encoding one or more of the polypeptides FspA1, FspA2, or fragments thereof. The expression system contemplated is capable of expressing in the selected bacteria carrier.

REFERENCES

1. Bolla, J. M., E. De, A. Dorez, and J. M. Pages. 2000. Purification, characterization and sequence analysis of Omp50, a new porin isolated from *Campylobacter jejuni*. Biochem. J. 352:637-643.
2. Burnens, A., U. Stucki, J. Nicolet, and J. Frey. 1995. Identification and characterization of an immunogenic outer membrane protein of *Campylobacter jejuni*. J. Clin. Microbiol. 33:2826-2832.
3. Carrillo, C. D., E. Taboada, J. H. E. Nash, P. Lanthier, J. Kelly, P. C. Lau, R. Verhulp, O. Mykytezuk, J. Sy, W. W. Findlay, K. Amoako, S. Gomis, P. Willson, J. W. Austin, A. Poter, L. Babiuk, B. Allan and C. M. Szymanski. 2004. Genome-wide Expression analyses of *Campylobacter jejuni* NCTC 11168 reveals coordinate regulation of motility and virulence by flhA. J. Biol. Chem. 279 (19):20327-20338.
4. Cover, T. L. and M. J. Blaser. 1999. The pathobiology of *Campylobacter* infections in humans. Ann. Rev. Med. 40:269-185.
5. Cortes-Bratti, X., C. Karlsson, T. Lagergard, M. Thelestam and T. Frisan. 2001. The *Haemophilus ducreyi* cytolethal distending toxin induces cell cycle arrest and apoptosis via DNA damage checkpoint pathways. Infect. Immun. 276: 5296-5302.
6. Gelfanova, V., E. J. Hansen, and S. M. Spinola. 1999. Cytolethal distending toxin of *Haemophilus ducreyi* induces apoptotic death of Jurkat T cells. Infect. Immun. 67:6394-6402.
7. Goon, S., C. P. Ewing, M. Lorenzo, D. Pattarini, G. Majam, and P. Guerry. 2006. A $\sigma^{28}$-regulated nonflagella gene contributes to virulence of *Campylobacter jejuni* 81-176. Infect. Immun. 74: 769-772.
8. Guerry, P., R. Alm, C. M. Szymanski and T. J. Trust. 2000. in *Campylobacter* (Nachamkin, I., and Blaser, M. J., eds) pp. 405-422, American Society for Microbiology, Washington, D.C.

9. Guerry, P., L. H. Lee, E. Burg, T. J. Trust. U.S. Pat. No. 6,987,176 issued Jan. 17, 2006.
10. Hendrixson, D. R., B. J. Akerley, V. J. DiRita. 2001. Transposon mutagenesis of *Campylobacter jejuni* identifies a bipartite energy taxis system required for motility. Mol. Microbiol. 40:214-224.
11. Hickey, T. E., A. L. McVeigh, D. A. Scott, R. E. Michielutti, A. Bixby, S. A. Carroll, A. Louis Bourgeois, and P. Guerry. 2000. *Campylobacter jejuni* cytoletal distending toxin mediates release of interleukin 8 from intestinal epithelial cells. Infect. Immun. 68:6535-6541.
12. Hickey, T. E., G. Majam and P. Guerry. 2005. Intracellular survival of *Campylobacter jejuni* in human monocytic cells and induction of apoptotic death by cytolethal distending toxin. Infect. Immun. 73:5194-5197.
13. Kuroki, S., T. Haruta, M. Yoshioka, Y. Kobayaski, M. Nukina, and H. Nakanishi. 1991. Guillain-Barre syndrome associated with *Campylobacter* infection. Pediatr. Infect. Dis. 10:149.
14. Macnab, R. M. 2003. How bacteria assemble flagella. Annu. Rev. Microbiol. 57:77 100.
15. Parker, C. T., B. Quinones, W. G. Miller, S. T. Horn and R. E. Mandrell. 2006. Comparative geneomic analysis of *Campylobacter jejuni* strains reveals diversity due to genomic elements similar to those present in *Campylobacter jejuni* strain RM 1221. J. clin. Microbiol. 44:4125-4135.
16. Parkhill, J., B. W. Wren, K. Mungall, J. M. Ketley, C. Churcher, D. Basham, T. Chillingworth, R. M. Davies, T. Feltwell, S. Holroyd, K. Jagels, A. V. Karlyshev, S. Moule, M. J. Pallen, C. W. Penn, M. A. Quail, M. A. Rajandream, K. M. Rutherford, A. H. van Vliet, S. Whitehead, and B. G. Barrell. 2000. The genome sequence of the food-borne pathogen *Campylobacter jejuni* reveals hypervariable sequences. Nature 403:665 668.
17. Poly, F., D. Threadgill, and A. Stintzi. 2005. Genomic diversity in *Campylobacter jejuni*: identification of *C. jejuni* 81-176 specific genes. J. Clin. Microbiol. 43:2330-2338.
18. Poly, F., D. Threadgill, and A. Stintzi. 2004. Identification of *Campylobacter jejuni* ATCC 43431-specific genes by whole microbial genome comparisons. J. Bacteriol. 186: 4781-4795.
19. Song, Y. C., S. Jin, H. Louie, D. Ng, R. Lau, Y. Zhang, R. Weerasekera, S. Al Rashid, L. A. Ward, S. D. Der and V. L. Chan. 2004. FlaC, a protein of *Campylobacter jejuni* TGH9011 (ATCC43431) secreted through the flagellar apparatus, binds epithelial cells and influences cell invasion. Mol. Microbiol. 53:541-553.
20. Tauxe, R. V. (1992) Epidemiology of *Campylobacter jejuni* infections in the United States and other industrialized nations. In *Campylobacter jejuni: Current status and future trends* (Edited by Nachamkin I., Blaser M. J. and Tompkins L. S.), p. 9. American Society for Microbiology, Washington, D.C.
21. Taylor, D. N. (1992) *Campylobacter* infections in developing countries. In *Campylobacter jejuni: Current status and future trends* (Edited by Nachamkin I., Blaser M. J. and Tompkins L. S.), p. 20. American Society for Microbiology, Washington, D.C.
22. Wassenaar, T. M., N. M. C. Bleumink-Pluym, and B. A. M. van der Zeijst. 1991. Inactivation of *Campylobacter jejuni* flagellin genes by homologous recombination demonstrates that flaA but not flaB is required for invasion. EMBO J. 10:2055-2061.
23. Yao, R., D. H. Burr, P. Doig, T. J. Trust, H. Niu, and P. Guerry. 1994. Isolation of motile and non-motile insertinal mutants of *Campylobacter jejuni*: the role of motility in adherence and invasion of eukaryotic cells. Mol. Microbiol. 14:883-893.

Having described the invention, one of skill in the art will appreciate in the appended claims that many modifications and variations of the present invention are possible in light of the above teachings. It is therefore, to be understood that, within the scope of the appended claims, the invention may be practiced otherwise than as specifically described.

What is claimed is:

1. An immunogenic composition comprising an isolated *Campylobacter jejuni* flagella secreted protein A, comprising amino acid sequence set forth in SEQ ID NO. 4.

2. The immunogenic composition of claim 1, wherein said flagella secreted protein A is a recombinant polypeptide.

3. The immunogenic composition of claim 2, wherein said polypeptide contains a histidine tag.

4. The immunogenic composition of claim 2, wherein said polypeptide is encoded by the nucleic acid sequence set forth in SEQ ID No. 3.

5. The immunogenic composition of claim 3, wherein said polypeptide is set forth in SEQ ID No. 16.

6. The immunogenic composition of claim 5, wherein said polypeptide is encoded by the nucleic acid sequence set forth in SEQ ID No. 15.

7. A method of inducing an immune response against *Campylobacter jejuni* comprising the steps of administering a dose of said immunogenic composition of claim 1.

8. The method of claim 7, comprising the addition step of administering one or more boosting doses subsequent to said priming dose wherein said boosting dose is comprised of the same said immunogenic composition as administered in said priming dose.

9. The method of claim 7, wherein said composition is a recombinant polypeptide with the amino acid sequence set forth in SEQ ID No. 4.

10. The method of claim 7, wherein said dose is administered by a method selected from the group consisting of intranasally, subcutaneously, transdermally, orally and intravenously.

11. The method of claim 8, wherein said boosting dose is administered by a method selected from the group consisting of intranasally, subcutaneously, transdermally, orally and intravenously.

12. The method of claim 9, wherein said recombinant polypeptide contains a histidine tag.

13. The method of claim 9 wherein said amino acid sequence is encoded by a nucleic acid sequence set forth in SEQ ID No. 3.

14. The method of claim 12, wherein said polypeptide is set forth in SEQ ID No. 16.

15. The method of claim 13, wherein said nucleotide sequences encoding said polypeptide sequences is inserted in an expression vector wherein said expression vector is selected from the group consisting of plasmid and viral expression vectors and wherein said expression vector is functional in mammalian subjects and wherein said polypeptide sequence is expressed.

16. The method of claim 13, wherein said nucleotide sequences are inserted in a plasmid or viral expression vector system and expressed in a live, attenuated strain of carrier bacteria.

17. The method of claim 16, wherein said attenuated strain of carrier strain is selected from the group consisting of *Escherichia coli*, member of the genus *Shigella*, member of the genus *Campylobacter*, member of the genus *Salmonella*, member of the genus *Vibrio*.

* * * * *